(12) United States Patent
Younis

(10) Patent No.: US 10,557,827 B2
(45) Date of Patent: Feb. 11, 2020

(54) ELECTROSTATICALLY ACTUATED TORSIONAL RESONANT SENSORS AND SWITCHES

(71) Applicant: KING ABDULLAH UNIVERSITY OF SCIENCE AND TECHNOLOGY, Thuwal (SA)

(72) Inventor: Mohammad Ibrahim Younis, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 198 days.

(21) Appl. No.: 15/575,962

(22) PCT Filed: Jun. 23, 2016

(86) PCT No.: PCT/IB2016/053756
§ 371 (c)(1),
(2) Date: Nov. 21, 2017

(87) PCT Pub. No.: WO2016/207834
PCT Pub. Date: Dec. 29, 2016

(65) Prior Publication Data
US 2018/0149619 A1    May 31, 2018

Related U.S. Application Data

(60) Provisional application No. 62/183,420, filed on Jun. 23, 2015.

(51) Int. Cl.
*G01N 29/02* (2006.01)
*G01N 29/036* (2006.01)
(Continued)

(52) U.S. Cl.
CPC ......... *G01N 29/022* (2013.01); *G01N 29/036* (2013.01); *G01N 29/2406* (2013.01);
(Continued)

(58) Field of Classification Search
CPC ............... G01N 29/022; G01N 29/036; G01N 29/2406; H01H 35/42; H01H 59/0009
(Continued)

(56) References Cited

U.S. PATENT DOCUMENTS

| 8,501,097 B1 | 8/2013 | Younis | |
| 2005/0173235 A1* | 8/2005 | Nielson | H01H 59/0009 200/181 |

(Continued)

OTHER PUBLICATIONS

Younis et al. "Exploration of New Concepts for Mass Detection in Electrostatically-Actuated Structures Based on Nonlinear Phenomena." Reasearchgate.net, Journal of Computational and Nonlinear Dynamics, Apr. 2009, www.researchgate.net. (Year: 2009).*

(Continued)

*Primary Examiner* — Nimeshkumar D Patel
*Assistant Examiner* — Jean F Morello
(74) *Attorney, Agent, or Firm* — Patent Portfolio Builers PLLC

(57) ABSTRACT

Embodiments in accordance of a torsional resonant sensor disclosure is configured to actuate a beam structure using electrostatic actuation with an AC harmonic load (e.g., AC and DC voltage sources) that is activated upon detecting a particular agent having a mass above a predefined level. In various embodiments, the beam structure may be different types of resonant structures that is at least partially coated or layered with a selective material.

20 Claims, 22 Drawing Sheets

(51) Int. Cl.
  *H01H 59/00*   (2006.01)
  *G01N 29/24*   (2006.01)
  *H01H 35/42*   (2006.01)

(52) U.S. Cl.
  CPC ........ *H01H 35/42* (2013.01); *H01H 59/0009* (2013.01); *G01N 2291/021* (2013.01); *G01N 2291/0255* (2013.01); *G01N 2291/0256* (2013.01); *G01N 2291/02809* (2013.01)

(58) Field of Classification Search
  USPC .......................................................... 73/657
  See application file for complete search history.

(56) References Cited

U.S. PATENT DOCUMENTS

| | | | |
|---|---|---|---|
| 2013/0047710 A1* | 2/2013 | Rhoads | G01N 29/022 73/64.53 |
| 2015/0192548 A1* | 7/2015 | Wilkinson | G01N 29/036 73/579 |

OTHER PUBLICATIONS

Bouchaala, A., et al., "Nonlinear-Based MEMS Sensors and Active Switches for Gas Detection," Sensors 2016, May 25, 2016, vol. 16, No. 758.

International Search Report in related International Application No. PCT/IB2016/053756, dated Sep. 21, 2016.

Nielson, G. N., et al., "Dynamic Pull-In of Parallel-Plate and Torsional Electrostatic MEMS Actuators," Journal of Microelectromechanical Systems, IEEE Service Center, USA, Aug. 2006, vol. 15, No. 4, pp. 811-821.

Vyas, A., et al., "Nonlinear Resonator with Interacting Flexural-Torsional Modes for Mass Sensing," Proceedings of the ASME 2007 International Design Engineering Technical Conferences & Computers and Information in Engineering Conference, IDETC/CIE 2007, Sep. 4-7, 2007, Las Vegas, Nevada, USA, vol. 1, Part B, pp. 967-973.

Written Opinion of the International Searching Authority in related International Application No. PCT/IB2016/053756, dated Sep. 21, 2016.

Younis, M. I., et al., "New Concepts of Mass Sensors Based on Lonlinear Dynamic Principles," Proceedings of the 11th International Congress and Exposition on Experimental and Applied Mechanics 2008, Jun. 2-5, 2008, Orlando, Florida, USA.

* cited by examiner

ELECTROSTATICALLY ACTUATED TORSIONAL RESONANT SENSORS AND SWITCHES

CROSS-REFERENCE TO RELATED APPLICATION

This application is a continuation of International Application No. PCT/IB2016/053756, filed Jun. 23, 2016, which claims priority to U.S. provisional application entitled "ELECTROSTATICALLY ACTUATED RESONANT SENSORS AND SWITCHES" having Ser. No. 62/183,420 filed on Jun. 23, 2015 which isare entirely incorporated herein by reference.

TECHNICAL FIELD

The present disclosure is related to microelectromechanical sensors and switches.

BACKGROUND

Resonant mass sensors refer to a category of devices in which a structure, typically a cantilever beam at the micro or nano scale, is excited to vibrate at resonance. The structure is coated and functionalized with a sensitive layer that has affinity to a specific vapor/gas, so that upon exposure to the vapor/gas, it can trap some of the vapor/gas on its surface. This leads to an increase of a total mass of the structure, thereby shifting its resonance frequency to a new value. This shift is taken as a measure of the captured mass of that vapor/gas.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

SUMMARY

Figure 1:
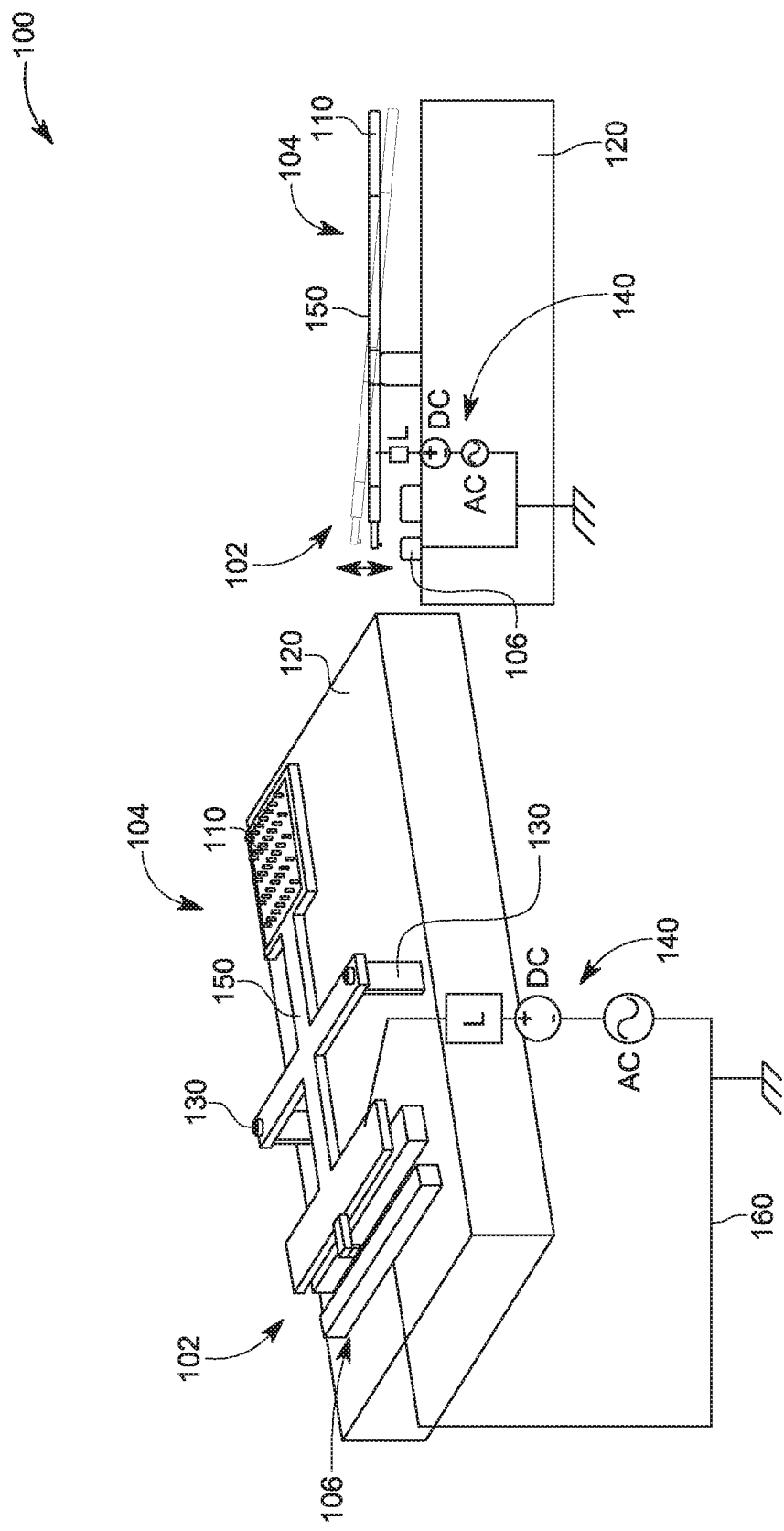
FIG. 1 is a diagram of perspective and side views of an embodiment of a torsional resonant sensor in accordance with the present disclosure.

Embodiments of the present disclosure provide systems, apparatuses, and methods for a torsional resonant sensor. In one such embodiment, a torsional resonator sensor apparatus comprises a resonator structure comprising a switching element and a sensor surface configured to detect a mass of a particular agent that becomes in contact with the sensor surface; AC and DC voltage sources that are coupled to the resonator structure and are configured to drive the resonator structure to resonate in a stable state at an operating frequency, wherein the resonator structure is configured to cause a resonance frequency shift for the resonator structure to lower values after contact of the particular agent with the sensor surface; and wherein the switching element is configured to be activated upon the contact of the sensor surface with the particular agent having a mass above a predefined level that causes the operating frequency to fall within a shifted pull-in frequency band for the resonator structure due to the contact of the particular agent with the sensor surface, wherein the switching element is configured to complete a circuit with a load element after being activated.

In any one or more aspects, the AC and DC voltage sources that are coupled to the switching element can be configured to activate the load element to signal detection of the particular agent. The apparatus can further comprise a load element. The load element can comprise an alarm. The sensor surface can comprise a metal-organic framework (MOF) for mass detection of the particular agent. The sensor surface can comprise a polymer material. The particular agent can comprise a gas, vapor, and/or biological entity. The resonator structure can comprise a torsional beam supported at a center area of the torsional beam by a support member. The resonator structure can have a first side and a second side, wherein the first side comprises the sensor surface and the second side comprises a switching element. The operating frequency can comprise a fixed frequency below a pull-in frequency band for the second side of the resonator structure. The switching element can comprise an upper electrode having an electrostatic charge contributed from the AC and DC voltage sources separated from a lower electrode, wherein the upper electrode comprises the second side of the resonator structure. Upon the sensor surface detecting the particular agent, the resonator structure can be configured to have its resonance frequency decrease and cause a pull-in frequency band for the second side to shift to lower values such that the operating frequency lies in the shifted pull-in frequency band causing the switching element to be actuated after collapse of the upper electrode. The apparatus can comprise a monitor device that is configured to detect the resonance frequency shift for the resonator structure and determine a mass of the particular agent based at least in part on the detected resonance frequency shift. The resonator structure can comprise a microbeam structure supported by fixed anchors at opposing sides of the microbeam structure, wherein the microbeam structure comprises an upper electrode of the switching element having the sensor surface that is configured to contact a lower electrode of the switching element upon activation of the switching element.

The present disclosure further describes embodiments of methods for a torsional resonant sensor. In one embodiment, one such method comprises providing a resonator structure comprising a sensor surface configured to detect a mass of a particular agent that becomes in contact with the sensor surface and a switching element; coupling AC and DC voltage sources to the resonator structure that are configured to drive the resonator structure to resonate in a stable state at an operating frequency, wherein the resonator structure is configured to cause a resonance frequency shift for the resonator structure to lower values after contact of the particular agent with the sensor surface; and activating a switching element of the resonator structure upon the contact of the sensor surface with the particular agent having a mass above a predefined level that causes the operating frequency to fall within a shifted pull-in frequency band for the resonator structure due to the contact of the particular agent with the sensor surface, wherein the switching element is configured to complete a circuit with a load element after being activated.

In any one or more aspects of such a method, the AC and DC voltage sources that are coupled to the switching element can be configured to activate the load element to signal detection of the particular agent. The method can comprise increasing the DC voltage source to a level above the AC voltage source to initiate a softening behavior of a frequency response curve of the resonator structure. The method can comprise increasing the AC voltage source to a level above the DC voltage source to initiate a hardening behavior of a frequency response curve of the resonator structure. The method can comprise determining the resonance frequency shift for the resonator structure; and determining a mass of the particular agent based at least in part on the determined resonance frequency shift. The resonance frequency shift can be determined by at least linearly fitting an upper branch of a frequency response curve the resonator structure.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

DETAILED DESCRIPTION

An obstacle of resonant mass sensing is that despite the fact that parallel-plate electrostatic actuation is considered the simplest, most energy efficient, and most common actuation method in microelectromechanical systems (MEMS), its use in resonant sensors is almost impossible. This type of actuation method relies on bringing together two parallel-plate electrodes within a few micrometers in separation from each other, which introduces a dilemma for the following reasons.

The first reason involves high squeeze-film damping (SQFD) that suppresses resonant motion. As electrostatic force increases with the inverse of the separation squared between the two parallel-plate electrodes, SQFD also increases (with the inverse of the separation cubed). Accordingly, SQFD completely quenches resonance (i.e., the sharp response peak never appears). For resonance to appear using electrostatic force, the separation between the two parallel-plate electrodes has to be large (e.g., more than ten microns), which raises the actuation voltage to unrealistic levels (e.g., thousands of voltage).

The second reason is directed to short circuit and stiction problems. For example, functionalizing and coating the surface of the resonant structure, which also forms the upper parallel-plate electrode, involves a wetting process through either direct immersion of the structure in liquid or through depositing the liquid on its surface, which can lead to spilling outside the surface of the structure to the lower parallel-plate electrode. This leads to droplet formation bridging the structure (upper electrode) to the lower electrode, which induces strong capillary and adhesion forces. These forces glue the structure permanently to the lower electrode leading to stiction and failure of the device.

Embodiments in accordance with the present disclosure solve the above problems by utilizing a torsional resonant sensor. In particular, an embodiment, among others, of a torsional resonant sensor 100 of the present disclosure is configured to actuate a see-saw like structure from one side 102 (corresponding to a switching device) using electrostatic actuation with an AC harmonic load (e.g., AC and DC voltage sources 140), as represented in FIG. 1. It is noted that the AC harmonic load will resonate the whole see-saw or beam structure 150 at both sides.

The other side 104 of a structure of the torsional resonant sensor 100 is configured to carry a layer of selective material 110, such as, but not limited to, a functionalized surface area with metal-organic framework (MOF), organic-polymers, inorganic-semiconductor films, or other chemical sensors, for mass detection and is left hanging freely in air at a considerable distance from the structure substrate 120 via support members 130 having torsional hinges. In this way, an SQFD is left at minimum effect (e.g., only influential near the small electrode area 106 at the actuation side 102) while the majority of the motion is SQFD free. Coating the surface area at the other side 104 of the see-saw like structure or beam 150 with a layer of sensitive material 110 is not problematic, because the elevated distance from the substrate 120 prevents capillary and stiction issues. Hence, embodiments of the torsional resonant sensor 100 can be used for bio-sensing applications where the un-actuated side 104 of the torsional resonant sensor 100 can be immersed in liquid safely without short circuit or stiction problems.

Application of the sensitive material to the beam 150 allows a particular agent, such as a gas/vapor/substance (e.g., a biological entity), to bond or capture the sensitive material 110 and to change the mass of the beam 150. While the beam 150 is driven by AC and DC voltage load to vibrate/resonate in a stable state at a resonance frequency, the change in mass of the beam 150 changes the resonance frequency of the beam 150 to lower values. This change in frequency can then be measured and analyzed via device(s) monitoring changes in characteristics of the beam 150, such as surface stresses, vibrations, etc. by optical laser(s), sensitive diode(s), piezoresistive element(s), etc. From the measured frequency change, the amount of captured/bonded/absorbed mass can be determined. For example, the frequency shift is taken to be proportional to the quantity of the particular agent being captured on the sensitive material 110.

Figure 2A:
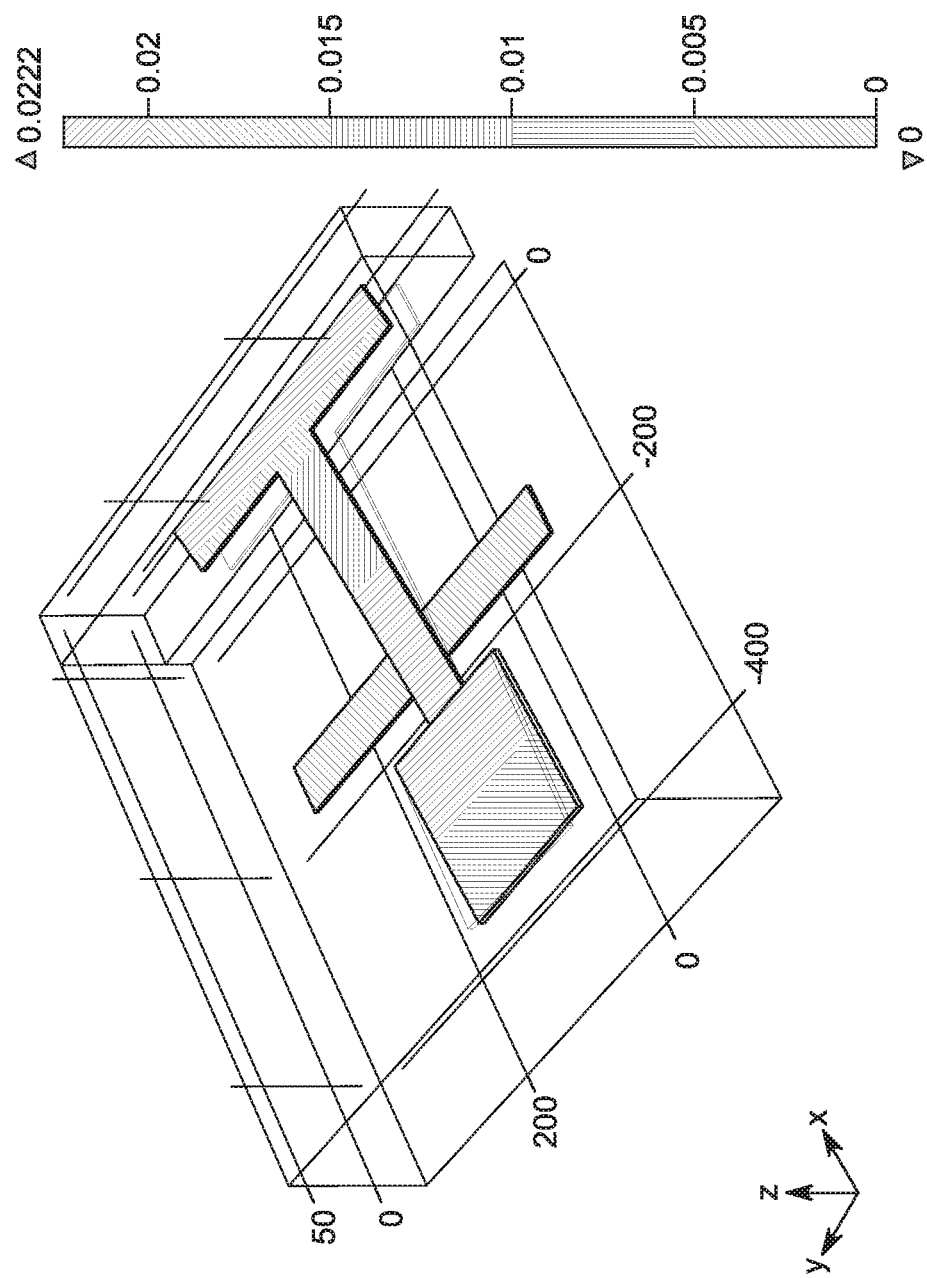
FIG. 2A is a diagram of an exemplary design of a torsional resonant sensor using finite element software COMSOL in accordance with an embodiment of the present disclosure.
Figure 2B:
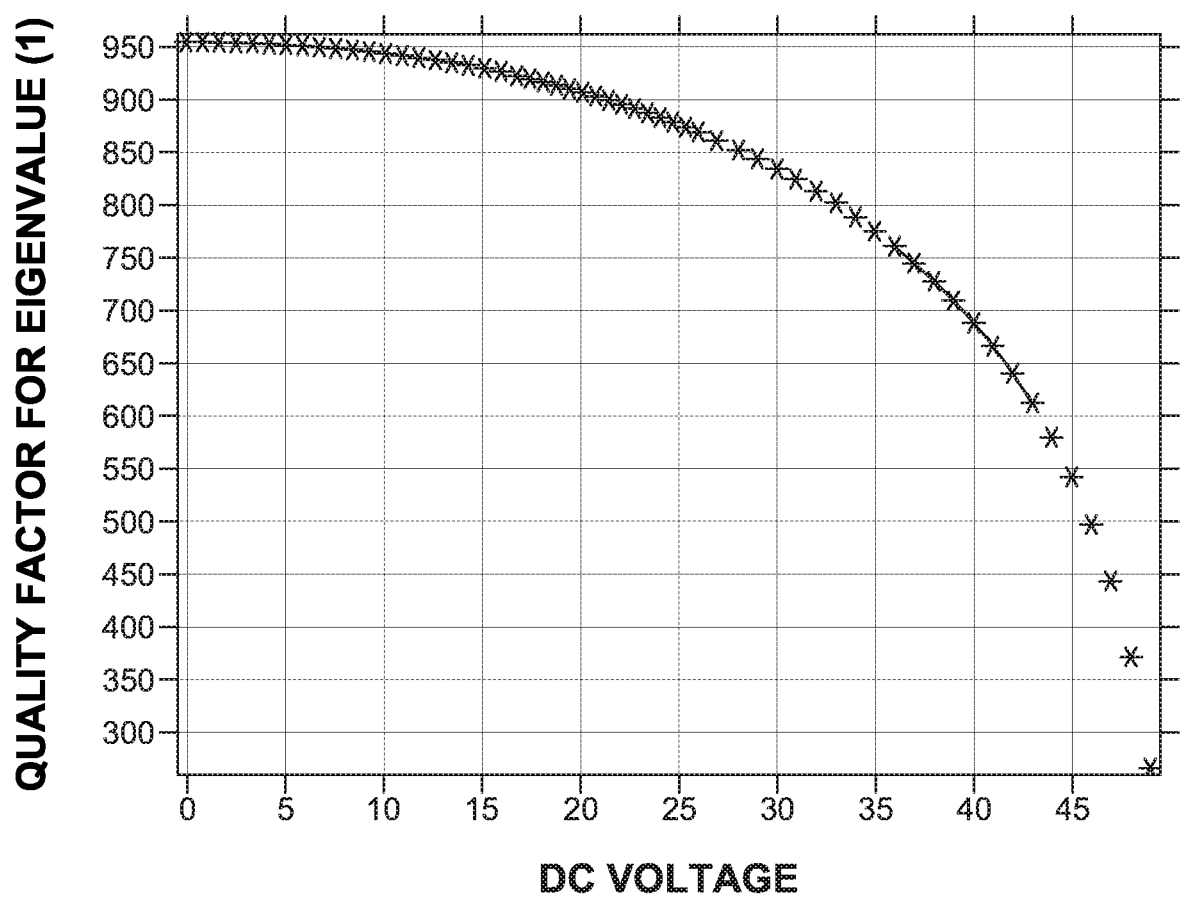
FIG. 2B is a chart of the quality factor performance in air for the exemplary design of FIG. 2A.

FIG. 2A shows a simulation of a performance of an exemplary design of the torsional resonant sensor 100 using finite element software COMSOL. Accordingly, using a multi-physics model accounting for electrostatic, fluidic, and structural domain, a high quality factor approaching 1000 in air is demonstrated in FIG. 2B for the exemplary torsional resonant sensor design due to its unique structural features. Further improvements in this number can be expected for various embodiments as the design is adjusted.

Various embodiments of the torsional resonant sensor 100 incorporate a smart threshold switch 102 (FIG. 1) that is triggered automatically upon the detection of a particular agent, such as a gas/vapor/substance (e.g., a biological entity) above a certain concentration threshold by the layer of sensitive material 110, e.g., a metal-organic framework (MOF), among others. Thus, the switching action can provide a decisive sign of detection and can be employed directly as an actuation signal to perform a desirable task via detection of an electrical signal by an attached load L (e.g., an alarm or alert signal).

An exemplary embodiment of the smart threshold switch 102 of the present disclosure is based on actuating a resonator structure or beam 150 by a large AC and DC voltage load 140 to generate an unstable band of frequency, referred as the pull-in frequency band. The resonator 150 is then operated at a fixed frequency below the pull-in band, so that the resonator 150 will vibrate in a stable state. When the side 104 of the resonator carrying the functionalized surface area with metal-organic framework (MOF) 110 detects a vapor/gas/substance, its natural frequency decreases, and hence, its pull-in band shifts to lower values.

By proper calibration, the resonator 150 is configured to shift its pull-in band such that the fixed excitation frequency lies within this band upon the detection of a certain pre-calibrated level of vapor/gas/substance. After the detection of this certain concentration level of the vapor/gas/substance, the other/actuator side 102 of the resonator 150 is configured to be forced to pull-in and collapse, thereby closing an electric circuit 160 (shown in FIG. 1 as an illustrative reference) via contacts of an upper electrode of the resonator 150 with a lower electrode 106 and passing a current as an electrical switch across the respective electrodes. Accordingly, an upper electrode of the resonator 150 having an electrostatic charge contributed from the AC and DC voltage sources 140 separated from a lower electrode 106 is caused to collapse and make contact with the lower electrode 106 due to pull-in forces.

Figure 3:
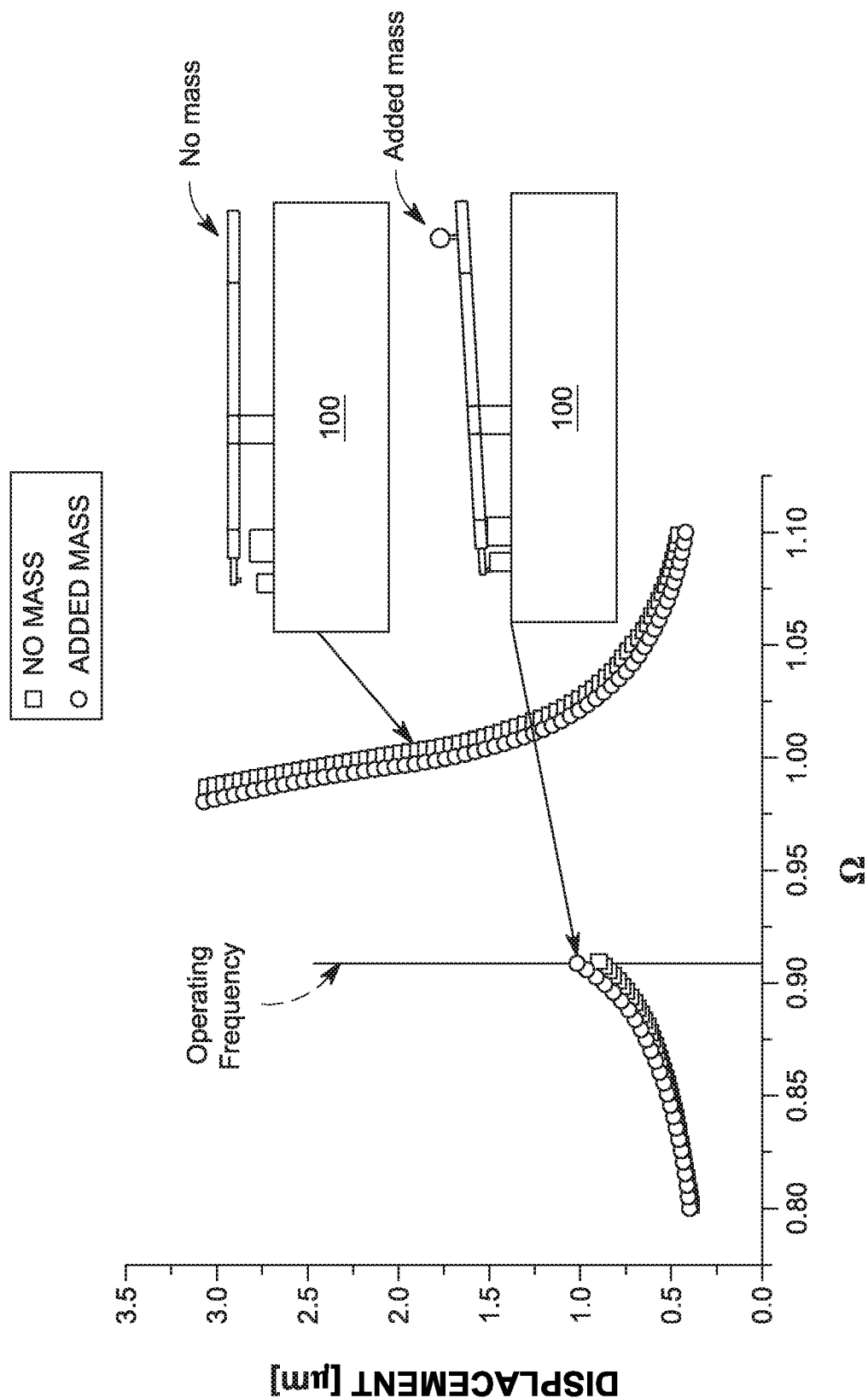
FIG. 3 is a chart demonstrating simulation of the response of the torsional resonant sensor before and after a uniform mass increase in accordance with an embodiment of the present disclosure.

Correspondingly, FIG. 3 demonstrates simulation of the response of the torsional resonant sensor 100 before and after a uniform mass increase in accordance with an embodiment of the present disclosure. In particular, the figure shows a simulated frequency-response curve showing dynamic pull-in bands for the actuator side of the smart threshold switch 102 before and after mass detection for the functionalized surface area with metal-organic framework (MOF) 110. Accordingly, the figure illustrates operation of the smart threshold switch 102 at a fixed excitation frequency (approximately 0.91 Hertz).

Unlike traditional monitoring systems, a smart threshold switch 102 in accordance with embodiments of the torsional resonant sensor 100 does not require complicated circuitry and decision units. Further, it does not require a complicated fabrication process (e.g., a standard MEMS procedure may be performed to realize a capacitor). In addition, the power consumption of this type of device, as the case of most MEMS devices, is very low. This promising technology can be used to deploy sensors in sensitive places where vapor/gas/substance need to be checked and tracked.

Correspondingly, in one embodiment, a torsional resonant sensor 100 in the form of a clamped-clamped microbeam 410 (FIG. 4B) is coated with a thin MOF film 110. The integration of the MOF thin film 110 on electrostatically actuated microstructures can be implemented to realize a smart threshold switch 102 triggered by gas and a sensing algorithm based on amplitude tracking. In one embodiment, the electrostatically actuated clamped-clamped microbeam is fabricated and coated with HKUST-1 MOF. HKUST-1 MOF is also known as $Cu_3(btc)_2 \cdot xH_2O$ MOF (where btc is 1,3,5-benzenetricarboxylate).

In one embodiment, the smart threshold switch 102 in a form of an electromechanical switch can perform two functionalities. On one hand, it can work as a sensor and track the change in frequency before a sudden change in amplitude of a vibrating wave from the microbeam structure. On the other hand, it can work as an electrical switch (or as an actuator), which will be activated upon gas adsorption beyond a certain threshold. Such switches are promising for applications where immediate actions, such as alarming, are needed upon detection of certain dangerous gases. To enhance the sensitivity of detection, the torsional resonator of the microbeam structure may be scaled down to the sub-micron and nano scale, in some embodiments.

Figure 4A:
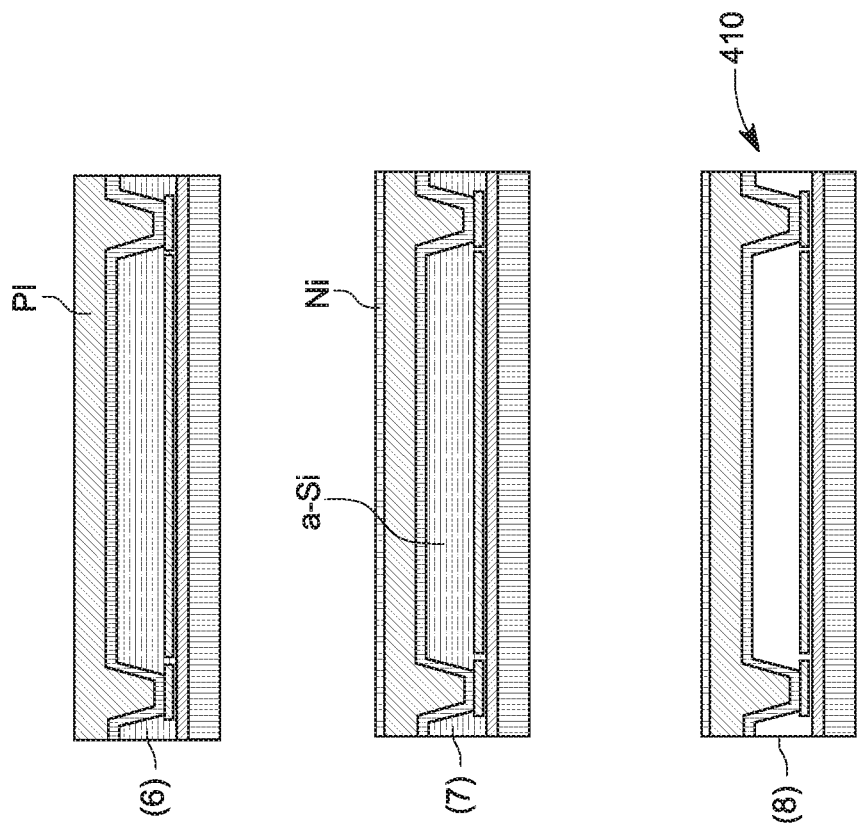
FIG. 4A is a diagram of an exemplary fabrication process flow for a torsional resonant sensor utilizing an electrostatically actuated clamped-clamped microbeam in accordance with an embodiment of the present disclosure.
Figure 4A:
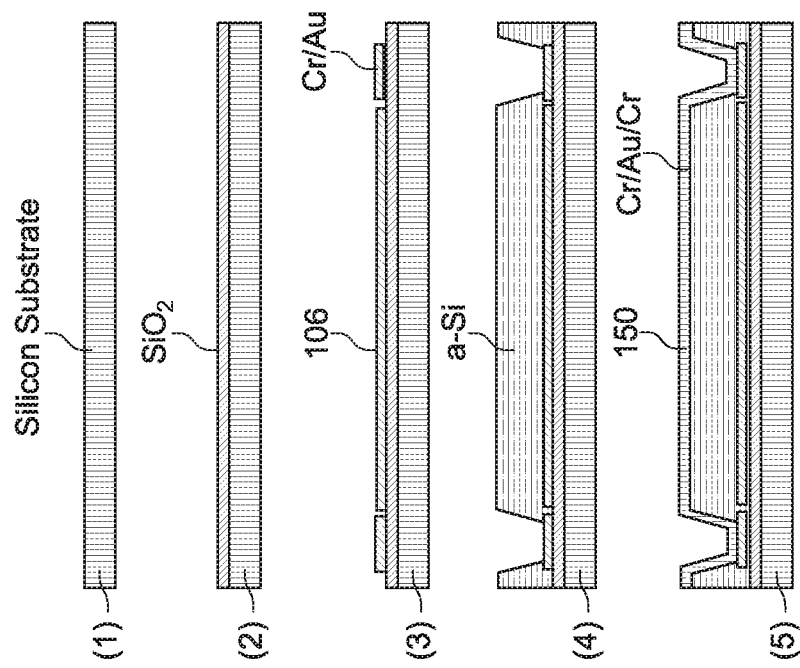
Figure 4B:
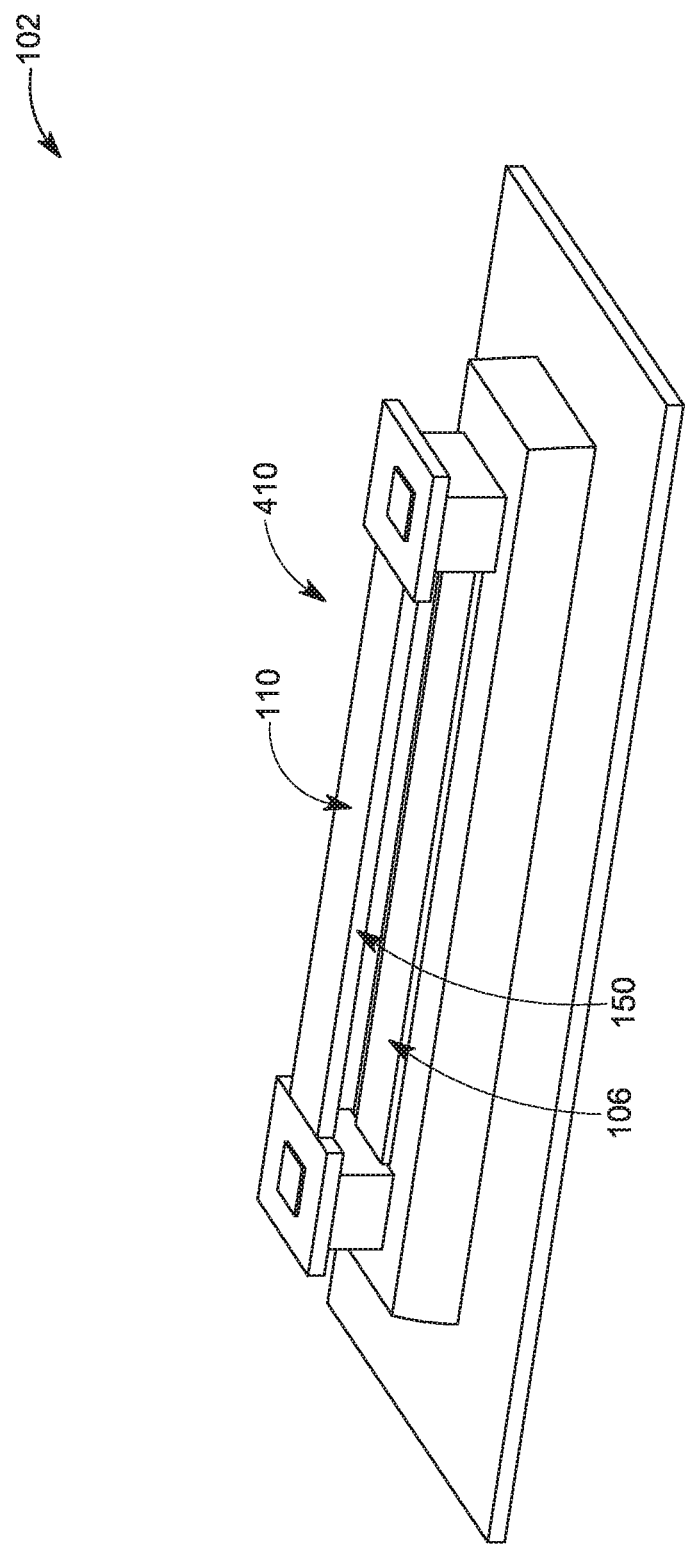
FIG. 4B is a schematic diagram of a torsional resonant sensor utilizing an electrostatically actuated clamped-clamped microbeam in accordance with an embodiment of the present disclosure.
Figure 4C:
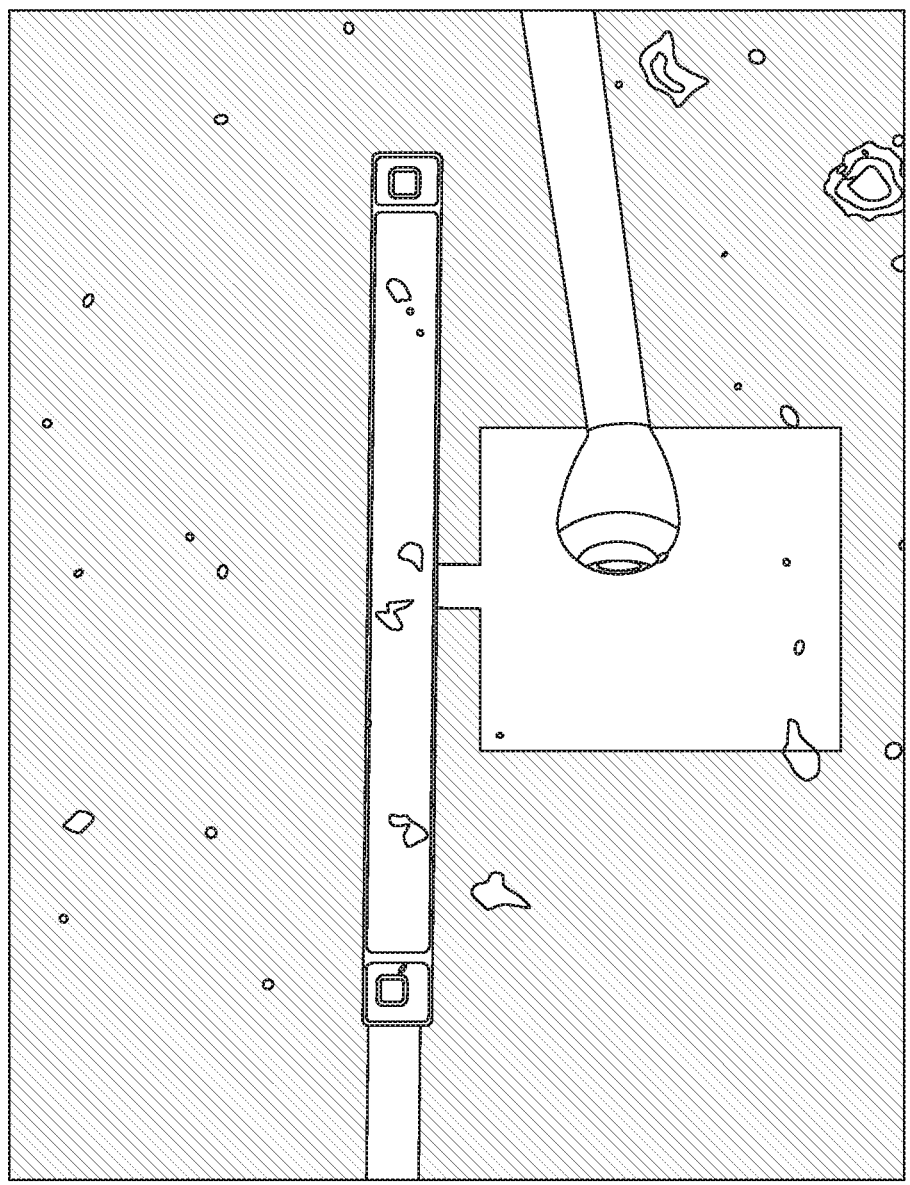
FIG. 4C is a diagram of an optical image of a fabricated clamped-clamped microbeam structure corresponding to FIGS. 4A and 4B in accordance with an embodiment of the present disclosure.

FIGS. 4A-4C represent an exemplary fabrication process flow, a schematic of the electrostatically actuated clamped-clamped microbeam 410, and an optical image of the fabricated clamped-clamped microbeam 410, respectively, in one embodiment. An exemplary clamped-clamped microbeam 410 may be fabricated using the fabrication process described in FIG. 4A. In such an embodiment, the process starts with a 4-inch silicon wafer (shown in step (1)) with a deposited silicon dioxide layer, which represents an insulation layer, as shown in step (2). The next step is to sputter the lower electrode 106, which is composed of a gold/chrome layer of thicknesses 250 nm/50 nm, in an exemplary embodiment, as shown in step (3) of FIG. 4A. Amorphous silicon is deposited on the top of the gold and chrome layers to form the sacrificial layer (a-Si). Two anchors are etched in the amorphous silicon layer to connect the upper electrode 150 with the lower connections as shown in step (4). In step (5), the upper electrode 150 is fabricated with chrome/gold/chrome layers of thicknesses 50 nm/250 nm/50 nm. Then in step (6), 6 μm of polyimide (PI) is spun and cured at gradually increasing temperature from 150° C. to 350° C. for 50 min and then held at 350° C. for 30 min to form the structural layer, in an exemplary embodiment. Finally, in step (7), a 500 nm nickel layer is sputtered on a top surface of the polyimide layer in order to protect the microbeam during the reactive ion etching, in step (8). The geometrical properties of the fabricated microbeam are shown below in Table 1 in accordance with an embodiment of the present disclosure.

TABLE 1

| Symbol | Quantity | Dimensions |
| --- | --- | --- |
| L | Length | 600 μm |
| h | Thickness | 6.85 μm |
| b | Width | 50 μm |
| d | Gap | 2 μm |

Next, an optical gas sensing setup that was used for exposing the MOF coated microstructure to water vapor during testing procedures is described. A high pressure nitrogen source is connected from one side to a bubbler, which contains the desired gas (water vapor) in liquid phase. The other side of the nitrogen source is connected to a flow meter controller to regulate the nitrogen flow when purging is needed to restore the frequency to its default value. The output of the bubbler is connected to a second flow meter to control the flow of the gas and the nitrogen mixture. A multifunction data acquisition card with the Labview program is utilized to control the flow rates. An environmental chamber is connected to the gas setup and is placed under the laser Doppler vibrometer from Polytec, Inc. (Mooresville, N.C., USA) in order to measure the microbeam deflection in real time. Additional information on the experimental setup is included in "Nonlinear-Based MEMS Sensors and Active Switches for Gas Detection" by Bouchaala, et al., published May 25, 2016, which is entirely incorporated herein by reference.

The flow mass controller connected to the bubbler is set to allow 0.4 L/min and 0.1 L/min of flow for jump-up and jump-down experiments, respectively. An inlet of the environmental chamber is connected to a pressure gauge to measure the pressure, which is equal to 3.3 Torr and 220 mTorr for jump-up and jump-down experiments, respectively (as discussed below).

During testing, frequency response curves of the coated clamped-clamped microbeam 410 were generated for various voltage loads. It is noted that a clamped-clamped microbeam 410 has two different sources of nonlinearities: the first one comes from mid-plane stretching due to the geometry of the structure and the fixed anchors. This nonlinearity is cubic and is dominant for low DC voltages, which leads to hardening behavior. The second source of nonlinearity is due to the electrostatic force, which is quadratic in nature, and leads to softening behavior. Next, frequency response curves of the beam for two representative flow rates, and hence, damping conditions, at various voltage loads are shown in the following figures.

Figure 5A:
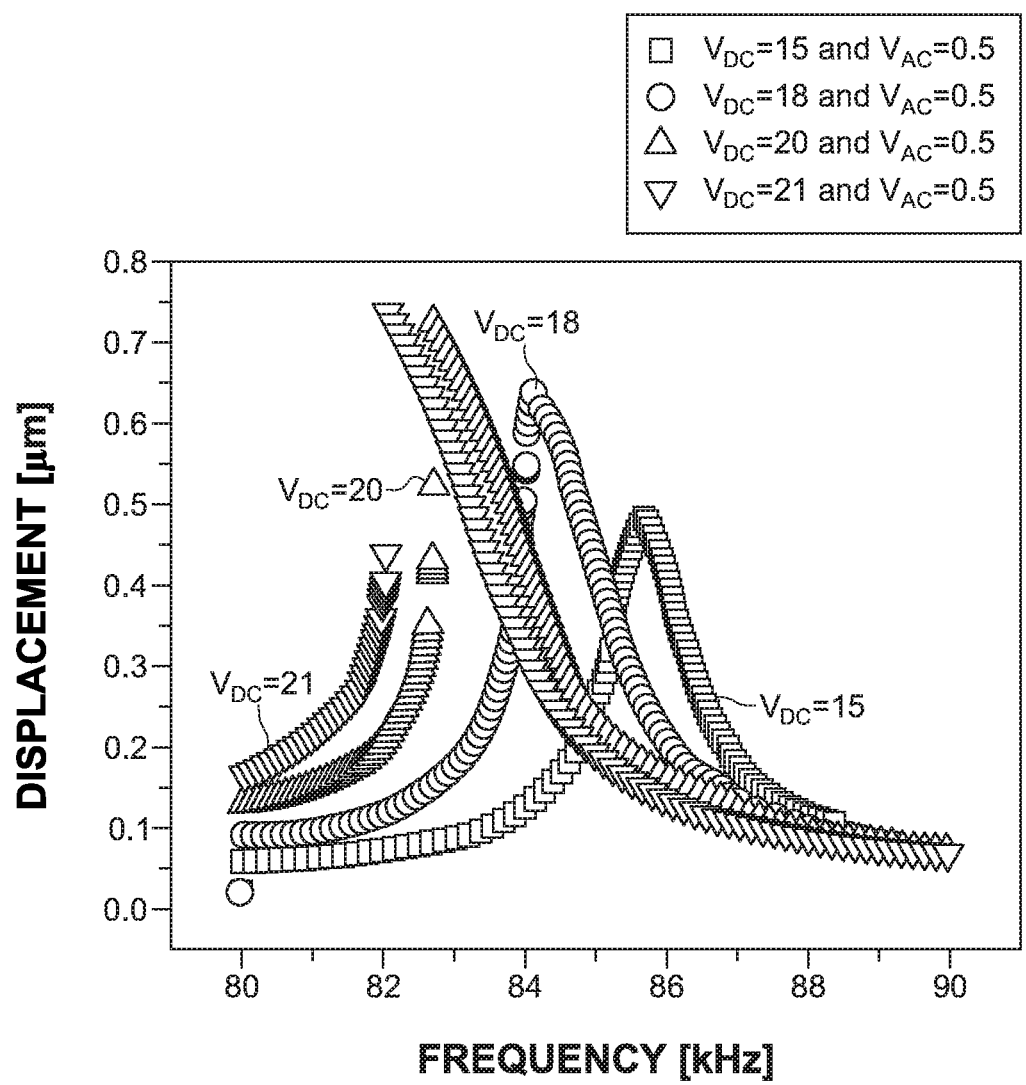
FIGS. 5A-5B are diagrams showing frequency response curves of the clamped-clamped microbeam structure corresponding to FIGS. 4A-4C for different DC values in accordance with an embodiment of the present disclosure.
Figure 5B:
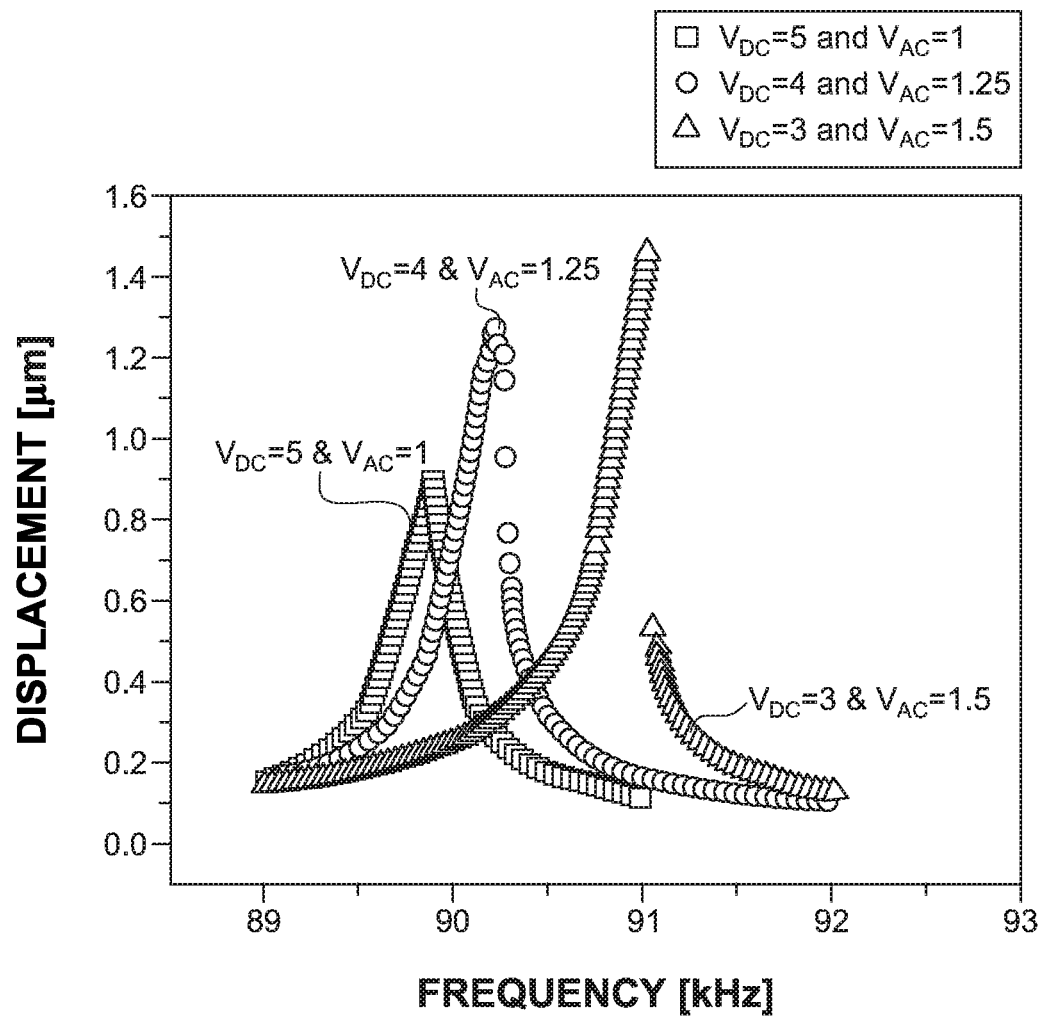

FIGS. 5A and 5B show the frequency response curves of the microbeam structure corresponding to FIGS. 4A-4C for different DC values. The microbeam characterization has been performed at the same conditions of the gas sensing experiments, which is at a pressure of 3.3 Torr. One can note that the effect of pressure is central here since it can change the nonlinear behavior, which is utilized in the clamped-clamped microbeam form of the torsional resonant sensor, into a linear behavior. In FIG. 5A, the black-square curve ($V_{DC}$=15 V and $V_{AC}$=0.5 V) represents the frequency response of the beam in the linear regime. By increasing the DC voltage, softening behavior starts to appear, and for some curves, this leads to hysteresis where two responses can exist at a single frequency. At $V_{DC}$=21 V and $V_{AC}$=0.5 V, a jump in the response of 0.3 μm occurs at the transition between the lower and upper dynamical states. This jump may be utilized for a smart threshold switch triggered by gas, in one embodiment. This type of smart threshold switch will be referred as a jump-up switch for purposes of this disclosure. Next, in FIG. 5B, increasing the AC voltage with a lower range of DC voltage leads to the appearance of the hardening behavior (the electrostatic nonlinearity here is too weak). The advantage of a hardening frequency response curve is that for a certain voltage load an almost linear segment of the upper branch of the frequency-response curve appears before jumping to the second lower branch. This segment can be used and fitted to a linear equation to track the amount of mass attached on the surface of the microbeam. Almost 1 μm jump in amplitude has been shown in FIG. 5B with $V_{DC}$=3 V and $V_{AC}$=1.5 V. This type of smart threshold switch will be referred as a jump-down switch.

Figure 6A:
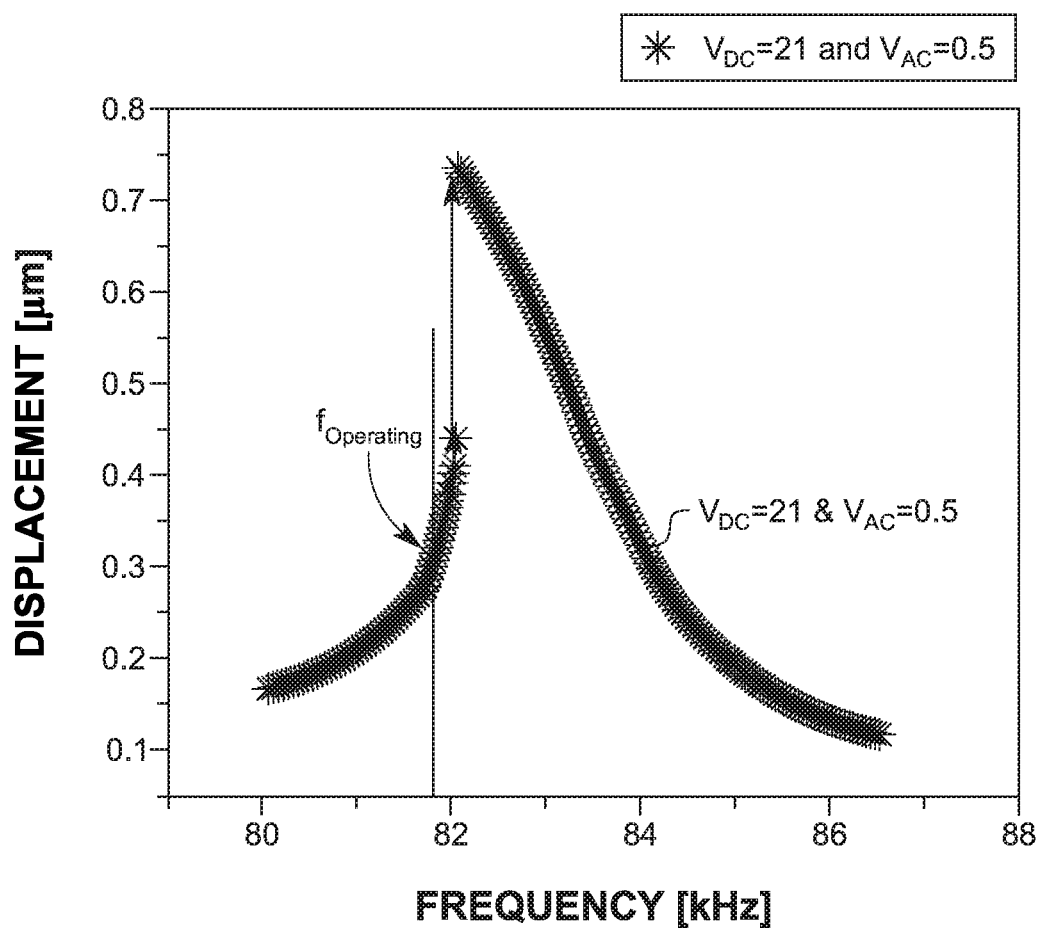
FIG. 6A is a diagram showing a frequency response for a smart threshold switch for a voltage load at $V_{DC}$=21 V and $V_{AC}$=0.5 V in accordance with an embodiment of the present disclosure.
Figure 6B:
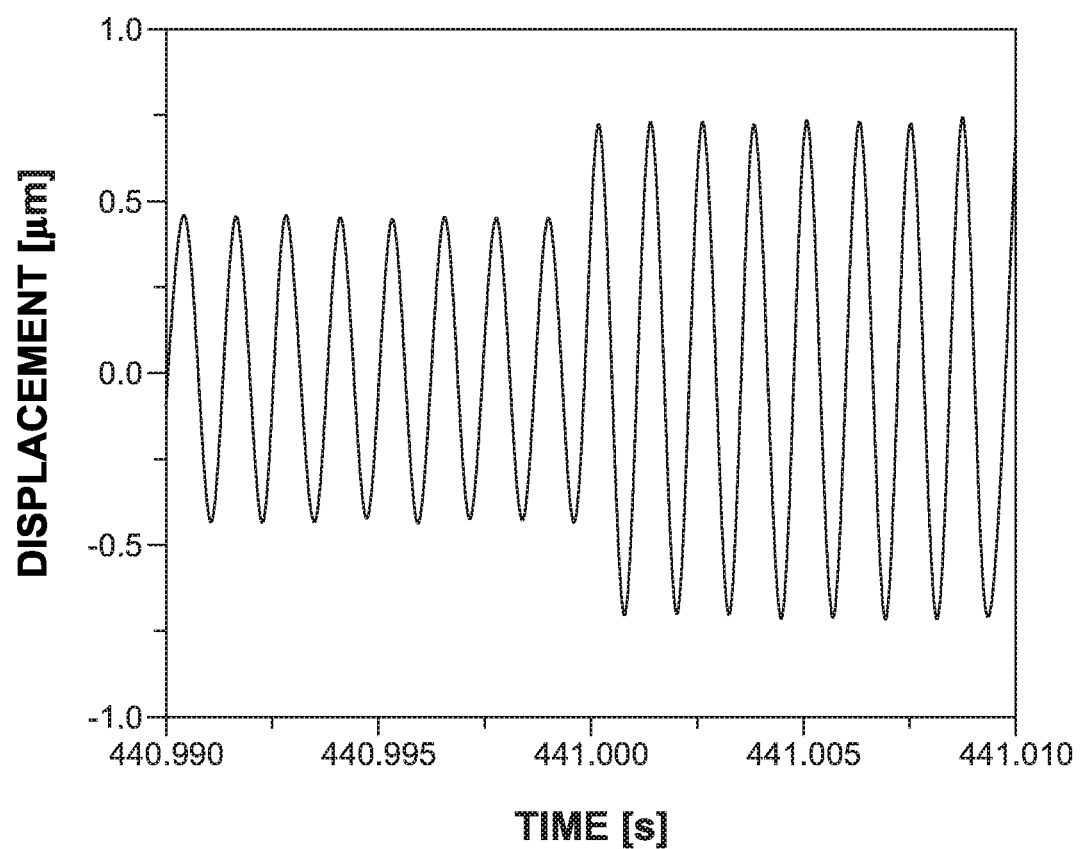
FIG. 6B is a diagram showing a time history of beam displacement upon gas exposure for the smart threshold switch of FIG. 6A in accordance with an embodiment of the present disclosure.

Next, a jump-up switch mechanism is detailed based on humidity detection. Before starting a water vapor sensing measurement, the microbeam 410 is flushed with nitrogen for an extended period of time to ascertain that the HKUST-1 MOF thin film 110 is activated, and the solvent has been evaporated, in order to start from a stable frequency reference. FIG. 6A represents the frequency response for the jump-up switch for $V_{DC}$=21 V and $V_{AC}$=0.5 V. In FIG. 6B, the time history of the mid-point of the microbeam 410 close to the jumping regime has been performed upon vapor exposure at a pressure of 3.3 Torr. The frequency response curve is shifted to a lower range of frequency and then at a certain point, the amplitude jumps-up suddenly. This abrupt change in amplitude is may be used for triggering the smart threshold switch 102, in one embodiment using a jump-up switch.

In addition to activating a jump-up switch based on the softening behavior for a high DC value, activating a jump-down switch based on the hardening behavior of a clamped-clamped microbeam 410 is featured in various embodiments of the present disclosure. The jump-down switch algorithm is the same as used for the jump-up switch, which relies on the sudden change in amplitude. However, in a jump-down switch, one can quantify the amount of absorbed mass prior to the sudden jump or the switching event as will be detailed next.

In order to demonstrate the jump-down switch during testing, a microcontroller from Arduino Inc. (Boston Mass., USA) equipped with an ATMEGA328P microprocessor was connected to the gas sensing setup. The outcome from the data acquisition card was connected to the microprocessor. A Labview program with an Arduino library was developed in order to read the voltage coming from the laser Doppler controller (Doppler vibrometer) at a fixed frequency. The algorithm is based on calculating the amplitude difference between two successive points during a frequency sweep. Therefore, when the absolute value of the difference between the current and previous data point exceeds a defined constant, switching is triggered.

Figure 7:
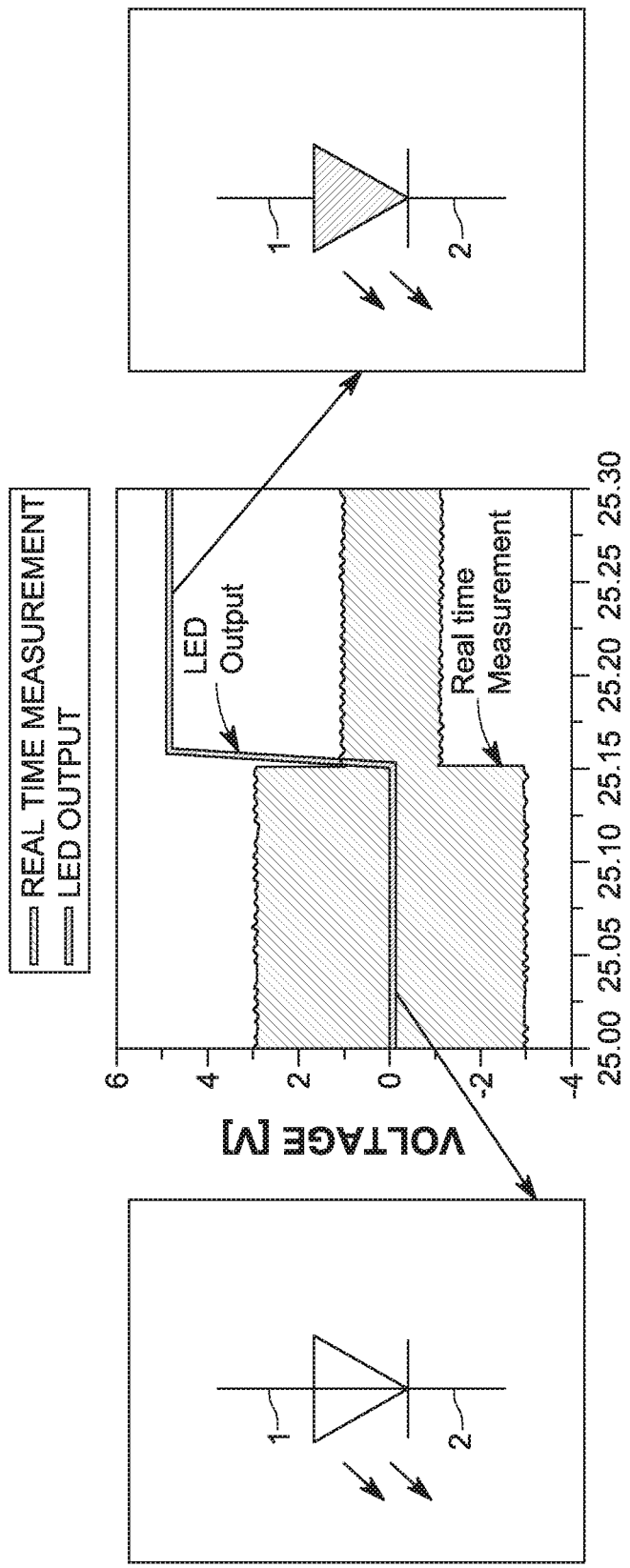
FIG. 7 is a diagram showing a time history of an exemplary torsional resonant sensor to trigger a LED upon water vapor exposure in accordance with an embodiment of the present disclosure.

An LED was connected to the Arduino digital output in order to indicate the switching upon gas adsorption. As shown in FIG. 7, the output voltage of the LED was tracked using a Labview program. When the jump occurs, the voltage is shown to have risen from 0 to 4.9 V, which represents the switching phenomenon.

Figure 8A:
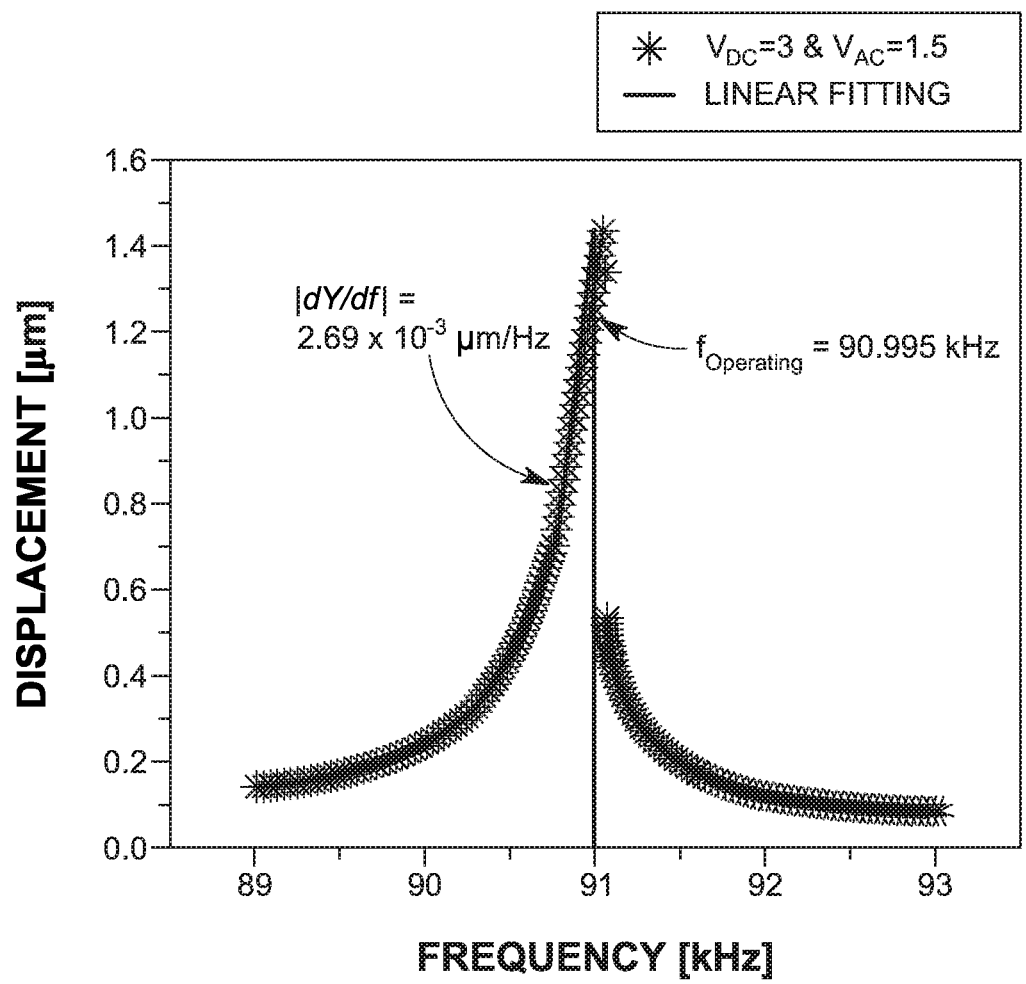
FIG. 8A is a diagram showing a frequency response for a smart threshold switch for a voltage load at $V_{DC}$=3 V and $V_{AC}$=1.5 V in accordance with an embodiment of the present disclosure.
Figure 8B:
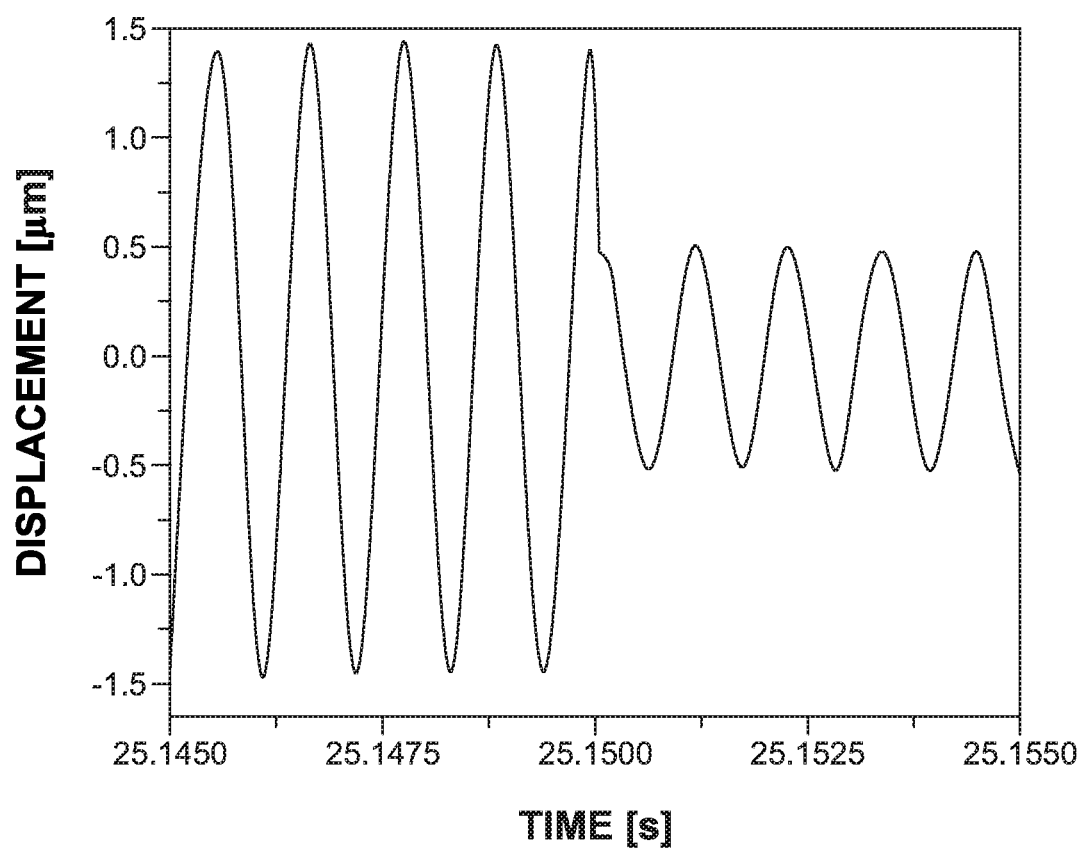
FIG. 8B is a diagram showing a time history of beam displacement upon gas exposure for the smart threshold switch of FIG. 8A in accordance with an embodiment of the present disclosure.

In FIG. 8A, the nonlinear frequency response is shown for $V_{DC}=3$ V and $V_{AC}=1.5$ V under a pressure of 220 mTorr. Using this set of conditions, the cubic nonlinearity dominates and the hardening behavior appears in the frequency response. The upper branch of the curve is linearly fitted (as discussed below) and can be used to relate the amplitude change to the frequency shift, and hence the amount of absorbed mass. In the vapor detection results shown in FIG. 8B, the same clamped-clamped microbeam 410 used for the previous gas sensing experiment with softening behavior has been utilized. However, the flow rate is set to be 0.1 L/min, which leads the pressure of the testing chamber to be equal to 220 mTorr.

Figure 9A:
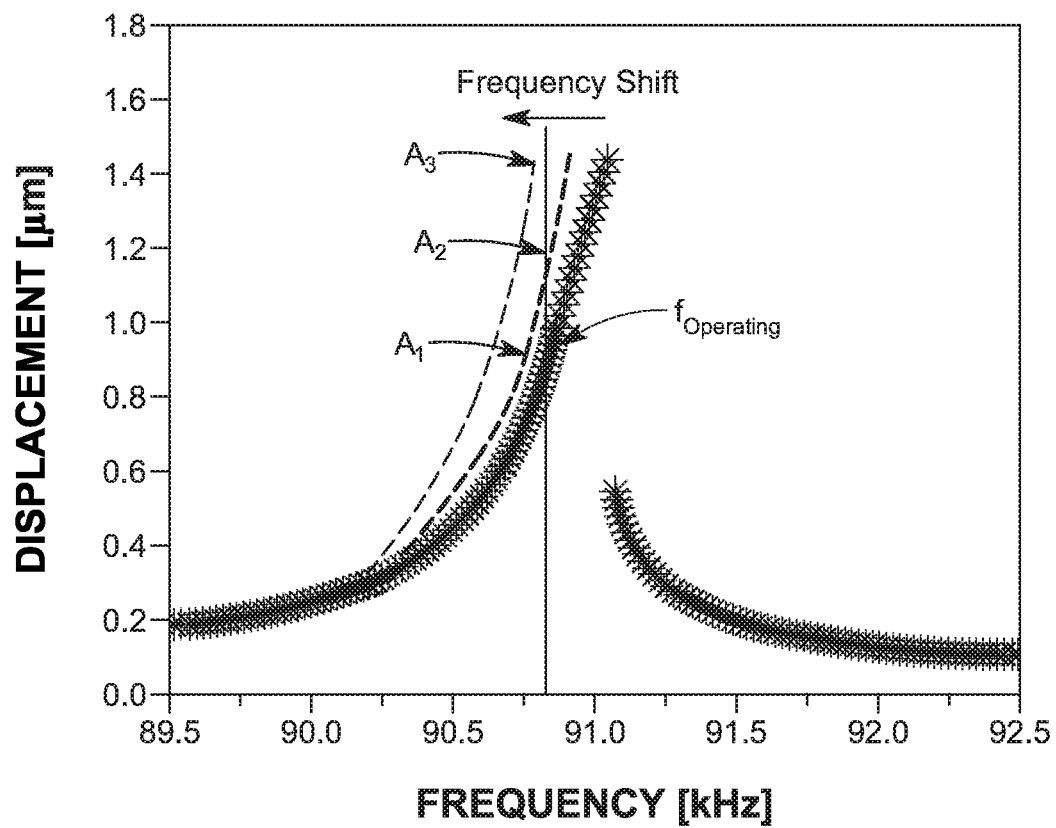
FIG. 9A is a diagram showing frequency responses for a smart threshold switch before and after water vapor exposure in accordance with an embodiment of the present disclosure.
Figure 9B:
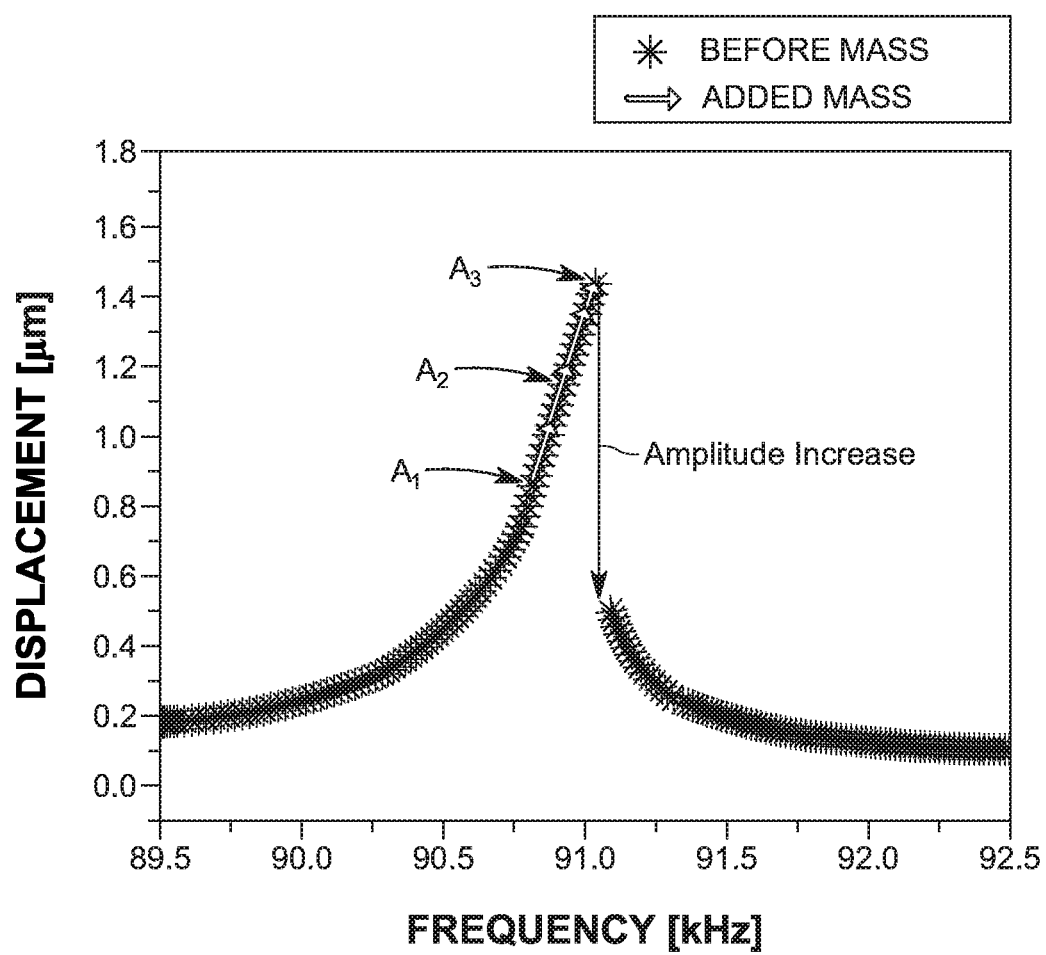
FIG. 9B is a diagram showing a single frequency response curve for a smart threshold switch before water vapor exposure in accordance with an embodiment of the present disclosure.
Figure 9C:
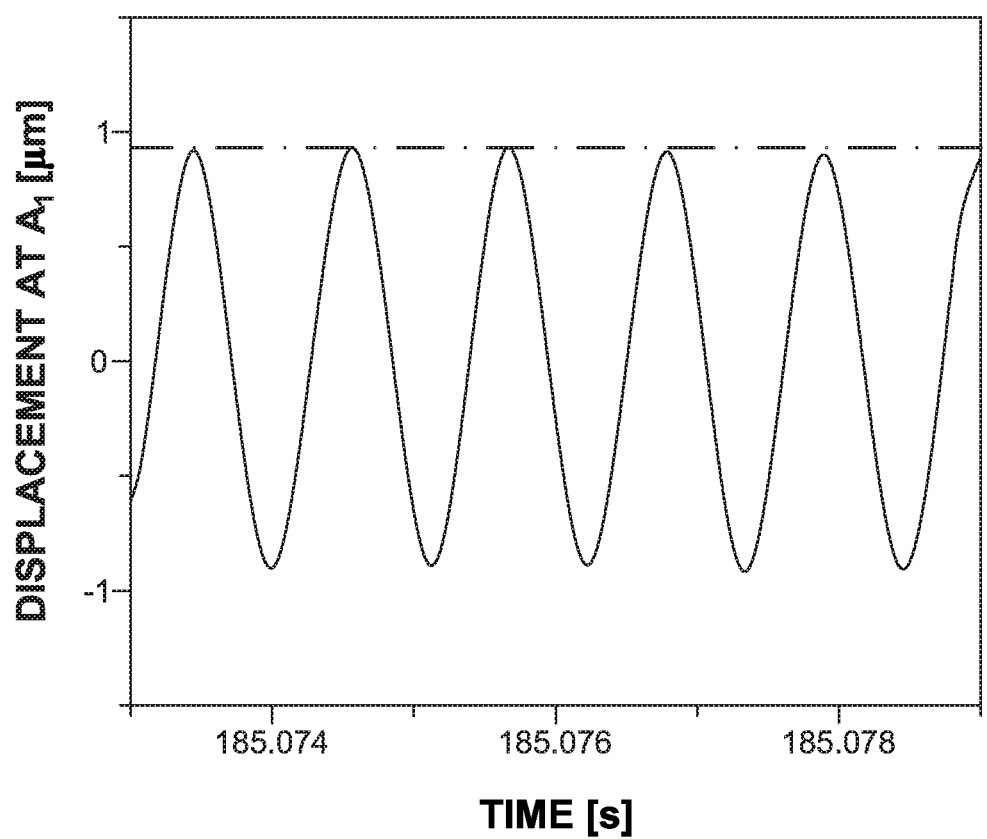
FIGS. 9C-9E are diagrams showing measured time history curves for respective displacement at points $A_1$, $A_2$, and $A_3$ of FIG. 9B in accordance with an embodiment of the present disclosure.
Figure 9D:
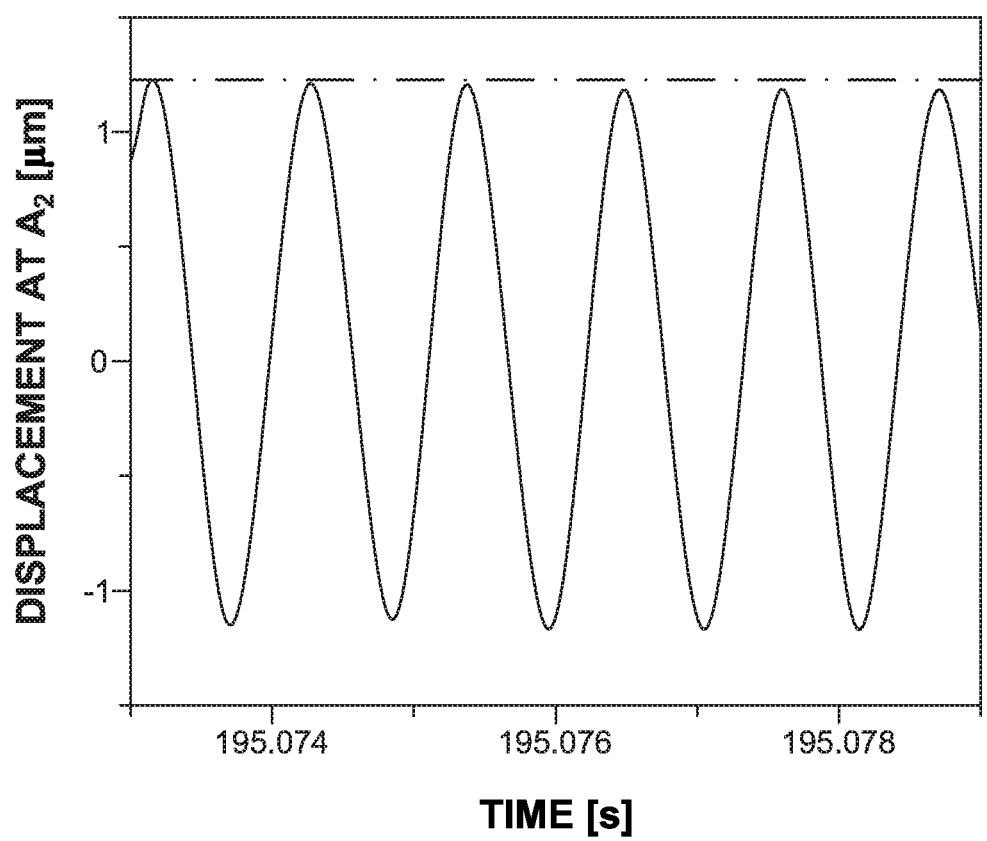
Figure 9E:
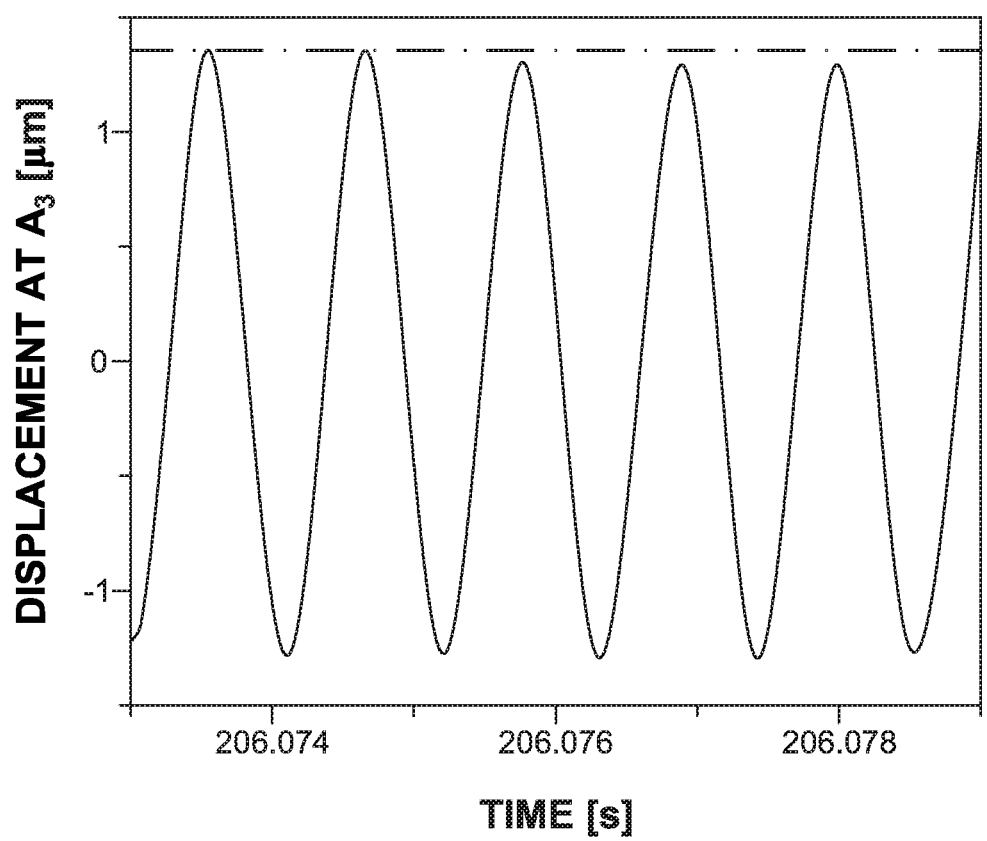

An approximate technique to quantify the adsorbed mass from linearly fitting the upper branch of the frequency response curve in the hardening behavior is described next. The concept relies on operating the resonator at a fixed frequency ($f_{Operating}$) before the jump-down regime in the frequency response curve, as shown in FIG. 9A. In the figure, the frequency response before vapor exposure is represented by the crisscrossed curve, and the frequency responses after vapor exposure is represented by the dashed curves. Since vapor exposure downshifts the frequency response curve, the amplitude at the fixed operating frequency line in FIG. 9A starts to increase, as illustrated through the different points of $A_1$, $A_2$, and $A_3$. FIG. 9A can be interpreted as an increase in amplitude along the linear branch of the frequency response, as shown in FIG. 9B. Then, at the fixed frequency $f_{Operating}$, the variation of the amplitude can be tracked as the microbeam is exposed to vapor as shown in FIGS. 9C-9E. This change in amplitude can be quantified and related/calibrated to the amount of captured mass.

Figure 10A:
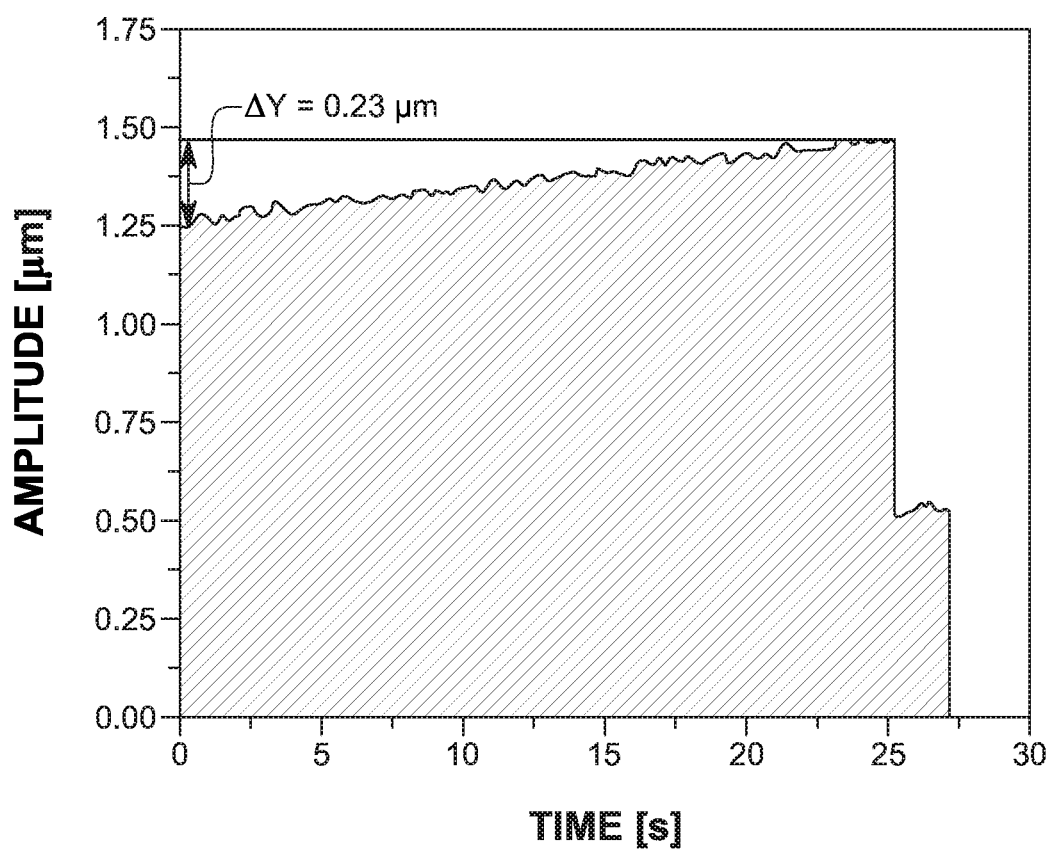
FIG. 10A is a diagram showing a measurement of amplitude variation upon gas exposure for a microbeam structure of a smart threshold switch in accordance with an embodiment of the present disclosure.

Now referring back to FIG. 8A, using a linear fitting, the slope of the linear branch is determined, which represents the variation of the amplitude with respect to the frequency $|dY/df|=2.69\times10^{-3}$ μm/Hz. Exposing the microbeam 410 to vapor leads to an increase in amplitude. This is further clarified in FIG. 10A, which shows a real time measurement of the microbeam mid-point deflection when exposed to water vapor. The amplitude of the fixed frequency $f_{Operating}=90.955$ kHz is equal to $Y_{Operating}=1.25$ μm before vapor exposure. After 25 seconds of vapor exposure, the amplitude of the point before jump (B-jump) reaches $Y_{B-Jump}=1.48$ μm, then it jumps-down.

Figure 10B:
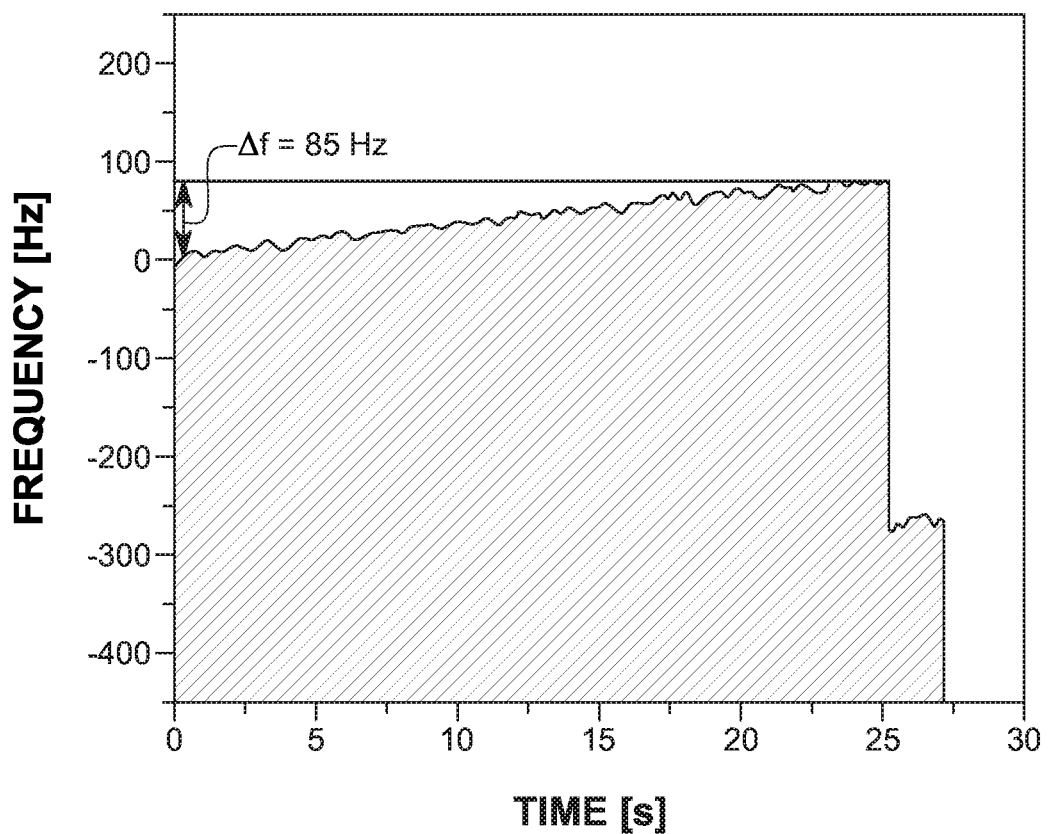
FIG. 10B is a diagram showing a measurement of frequency shift upon gas exposure for a microbeam structure of a smart threshold switch in accordance with an embodiment of the present disclosure.
Figure 10C:
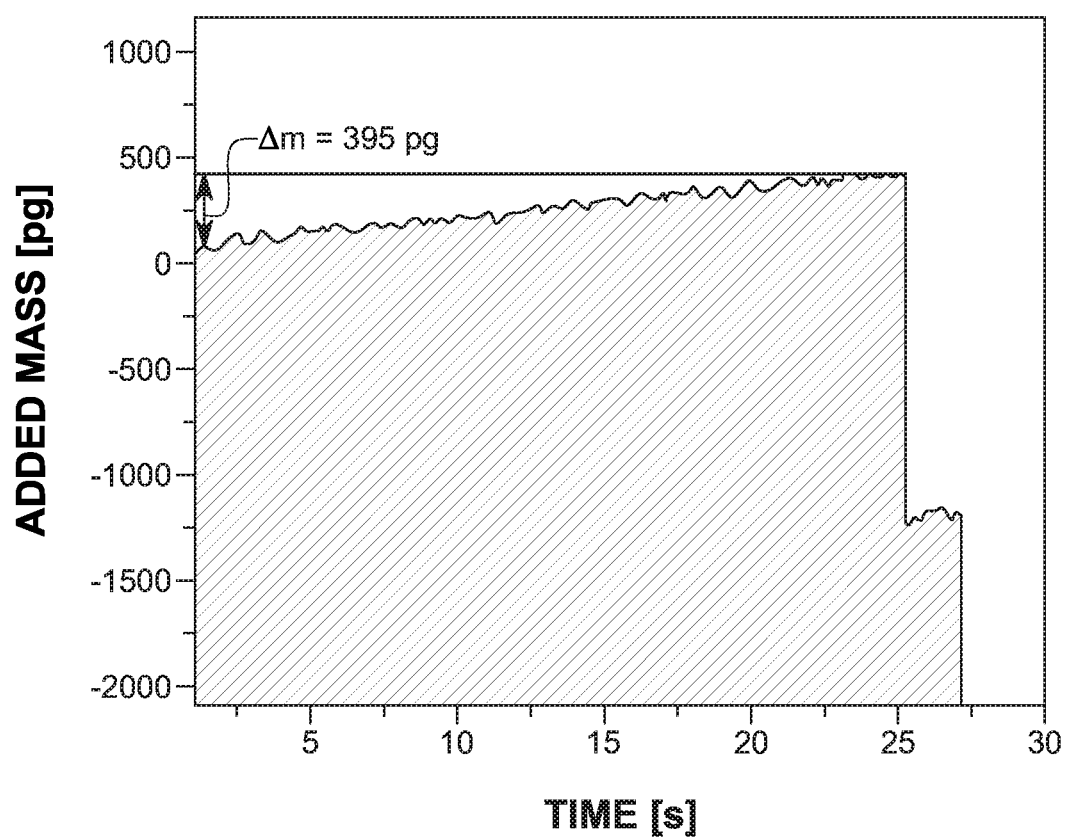
FIG. 10C a diagram showing a measurement of mass variation upon gas exposure for a microbeam structure of a smart threshold switch in accordance with an embodiment of the present disclosure.

The calculated slope of the linear branch is used to determine the frequency shift for the torsional resonant sensor as a function of time, as illustrated in FIG. 10B. The initial amplitude value is subtracted from the amplitude variation and then divided by the calculated slope. By measuring the frequency shift as a function of time (from FIG. 10B), $\Delta f=85$ Hz before reaching the jump zone. In order to check the accuracy of these calculations, the frequency shift coming from the real time measurement in FIG. 10B was compared with the frequency shift calculated from FIG. 8A by subtracting the frequency of the point just before the jump $f_{B-Jump}=91.04$ kHz from the operating frequency $f_{Operation}=90.955$ kHz. The least calculated frequency was found to be equal to $\Delta f=85.55$ Hz, which is very close to the calculated frequency shift using linear fitting. Then, the amount of the added mass $\Delta m$ can be tracked in real time from the induced frequency shift $\Delta f$ as shown in FIG. 10C. The total mass attached on an exemplary torsional resonant sensor before the activation of smart threshold switch is $\Delta m=395$ pg, in one embodiment using a jump-down switch. Additional information is included in "Nonlinear-Based MEMS Sensors and Active Switches for Gas Detection" by Bouchaala, et al., published May 25, 2016, which is entirely incorporated herein by reference.

It should be emphasized that the above-described embodiments are merely possible examples of implementations, merely set forth for a clear understanding of the principles of the present disclosure. Many variations and modifications may be made to the above-described embodiment(s) without departing substantially from the principles of the present disclosure. All such modifications and variations are intended to be included herein within the scope of this disclosure and protected by the following claims.

Therefore, at least the following is claimed:

1. A torsional resonator sensor apparatus comprising:
   a resonator structure comprising a beam suspended above a substrate, the beam having a switching element at an actuated end and a sensor surface at an un-actuated end, wherein the resonator structure is configured to detect a mass of a particular agent that becomes in contact with the sensor surface; and
   AC and DC voltage sources that are coupled to the resonator structure and are configured to drive the resonator structure to resonate in a stable state at an operating frequency, wherein the resonator structure is configured to cause a resonance frequency shift for the resonator structure to lower values after contact of the particular agent with the sensor surface,
   wherein the beam is suspended above the substrate with torsional support members so that (1) there is an electrode area located on the substrate, next to the actuated end, and (2) there is no electrode located on the substrate, next to the un-actuated end,
   wherein the torsional support members are attached to the beam between the actuated end and the un-actuated end, and
   wherein the switching element is configured to be activated upon the contact of the sensor surface with the particular agent having a mass above a predefined level that causes the operating frequency to fall within a shifted pull-in frequency band for the resonator structure due to the contact of the particular agent with the sensor surface.

2. The apparatus of claim 1, wherein the switching element is configured to complete a circuit with a load element after being activated, and wherein the AC and DC voltage sources that are coupled to the switching element are configured to activate the load element to signal detection of the particular agent.

3. The apparatus of claim 2, further comprising the load element.

4. The apparatus of claim 3, wherein the load element comprises an alarm.

5. The apparatus of claim 1, wherein the sensor surface comprises a metal-organic framework (MOF) for mass detection of the particular agent.

6. The apparatus of claim 1, wherein the sensor surface comprises a polymer material.

7. The apparatus of claim 1, wherein the particular agent comprises a gas, vapor, or biological entity.

8. The apparatus of claim 1, wherein the beam is supported at a center area of the beam by the support members.

9. The apparatus of claim 1, wherein the resonator structure has a first side and a second side, wherein the first side comprises the sensor surface and the second side comprises a switching element.

10. The apparatus of claim 9, wherein the operating frequency comprises a fixed frequency below a pull-in frequency band for the second side of the resonator structure.

11. The apparatus of claim 10, wherein the switching element comprises an upper electrode having an electrostatic charge contributed from the AC and DC voltage sources separated from a lower electrode, wherein the upper electrode comprises the second side of the resonator structure.

12. The apparatus of claim 11, wherein upon the sensor surface detecting the particular agent, the resonator structure is configured to have its resonance frequency decrease and cause a pull-in frequency band for the second side to shift to lower values such that the operating frequency lies in the shifted pull-in frequency band causing the switching element to be actuated after collapse of the upper electrode.

13. The apparatus of claim 1, further comprising a monitor device that is configured to detect the resonance frequency shift for the resonator structure and determine a mass of the particular agent based at least in part on the detected resonance frequency shift.

14. The apparatus of claim 1, wherein the resonator structure comprises a microbeam structure supported by fixed anchors at opposing sides of the microbeam structure, wherein the microbeam structure comprises an upper electrode of the switching element having the sensor surface that is configured to contact a lower electrode of the switching element upon activation of the switching element.

15. A method comprising:
providing a resonator structure comprising a beam suspended above a substrate, the beam having a sensor surface, at an un-actuated end of the beam, configured to detect a mass of a particular agent that becomes in contact with the sensor surface, and a switching element at an actuated end of the beam;
coupling AC and DC voltage sources to the resonator structure that are configured to drive the resonator structure to resonate in a stable state at an operating frequency, wherein the resonator structure is configured to cause a resonance frequency shift for the resonator structure to lower values after contact of the particular agent with the sensor surface; and
activating the switching element of the resonator structure upon the contact of the sensor surface with the particular agent having a mass above a predefined level that causes the operating frequency to fall within a shifted pull-in frequency band for the resonator structure due to the contact of the particular agent with the sensor surface, wherein the switching element is configured to complete a circuit with a load element after being activated,
wherein the beam is suspended above the substrate with torsional support members so that (1) there is an electrode area located on the substrate, next to the actuated end, and (2) there is no electrode located on the substrate, next to the un-actuated end, and
wherein the torsional support members are attached to the beam, between the actuated end and the un-actuated end.

16. The method of claim 15, wherein the AC and DC voltage sources that are coupled to the switching element are configured to activate the load element to signal detection of the particular agent.

17. The method of claim 16, further comprising increasing the DC voltage source to a level above the AC voltage source to initiate a softening behavior of a frequency response curve of the resonator structure.

18. The method of claim 16, further comprising increasing the AC voltage source to a level above the DC voltage source to initiate a hardening behavior of a frequency response curve of the resonator structure.

19. The method of claim 16, further comprising:
determining the resonance frequency shift for the resonator structure; and
determining a mass of the particular agent based at least in part on the determined resonance frequency shift.

20. The method of claim 19, wherein the resonance frequency shift is determined by at least linearly fitting an upper branch of a frequency response curve of the resonator structure.

* * * * *